United States Patent
Waldmann

(10) Patent No.: US 7,156,865 B2
(45) Date of Patent: Jan. 2, 2007

(54) IRRADIATION APPARATUS AND SYSTEM, ESPECIALLY FOR PHOTODYNAMIC THERAPY

(75) Inventor: Gerhard Waldmann, Dauchingen (DE)

(73) Assignee: Herbert Waldmann GmbH & Co. (DE)

( * ) Notice: Subject to any disclaimer, the term of this patent is extended or adjusted under 35 U.S.C. 154(b) by 754 days.

(21) Appl. No.: 10/265,838

(22) Filed: Oct. 7, 2002

(65) Prior Publication Data
US 2003/0088296 A1 May 8, 2003

(30) Foreign Application Priority Data
Oct. 8, 2001 (DE) .............................. 101 49 462

(51) Int. Cl.
*A61N 5/06* (2006.01)
(52) U.S. Cl. .......................................... 607/88; 607/91
(58) Field of Classification Search ............ 607/88–94; 901/14–15, 27
See application file for complete search history.

(56) References Cited

U.S. PATENT DOCUMENTS

| | | | | |
|---|---|---|---|---|
| 3,713,453 A * | 1/1973 | Chiaro et al. ................ | 132/212 |
| 3,809,454 A * | 5/1974 | Brambring .................. | 359/382 |
| 3,818,914 A * | 6/1974 | Bender ........................ | 607/90 |
| 3,850,307 A * | 11/1974 | Motoda ....................... | 212/237 |
| 4,068,156 A | 1/1978 | Johnson et al. | |
| 4,114,464 A * | 9/1978 | Schubert et al. ............ | 74/89.14 |
| 4,428,710 A * | 1/1984 | Grisebach et al. .......... | 414/590 |
| 4,458,870 A * | 7/1984 | Duncan et al. .......... | 248/279.1 |
| 4,463,413 A * | 7/1984 | Shirley ........................ | 362/401 |
| 4,473,074 A * | 9/1984 | Vassiliadis .................... | 606/19 |
| 5,257,998 A * | 11/1993 | Ota et al. .................... | 606/130 |
| 5,634,377 A * | 6/1997 | Kimura et al. ........... | 74/490.04 |
| 6,012,693 A * | 1/2000 | Voeller et al. ......... | 248/280.11 |
| 6,019,484 A * | 2/2000 | Seyler ........................ | 362/287 |

(Continued)

FOREIGN PATENT DOCUMENTS

DE      8813852.6      12/1988

(Continued)

*Primary Examiner*—Henry M Johnson, III
(74) *Attorney, Agent, or Firm*—Eugene E. Renz, Jr.

(57) ABSTRACT

To allow optimum adaptation of irradiation equipment, especially irradiation equipment for photodynamic therapy, to the individual anatomy of a patient, an irradiation head (1) is provided with a plate-shaped middle section (2) and plate-shaped lateral leaves (3), mounted on the middle section (2) in such a way that they can swivel. The irradiation head can be rotated about two perpendicular axes (U, W), and its height can be adjusted. With its lateral leaves (3) extended, the irradiation head (1) has a plane configuration formed by the middle section (2) and the extended lateral leaves (3). The configuration is suitable for areal irradiation of the trunk or extremities of a patient. It can also be configured to a rectangular U shape suitable for three-sided irradiation, when the lateral leaves (3) are swivelled 90°. Radiation sources, e.g., cylindrical or compact light fixtures, which have a spectrum from UV, through visible light, to IR and are preferably interchangeable, are provided in or on the undersides of the middle section (2) and the lateral leaves (3). The middle section (2) is mounted at one end of a preferably telescoping swivel arm (6) by means of a first swivel joint (5). A second swivel joint (7) is provided for mounting the other end of the swivel arm (6) on the upper end of a column (8), which is supported in a column support (9) in such a way that it can be moved along its longitudinal axis (Z) and rotated about its longitudinal axis (Z). The column support (9) is mounted, for example, on a control console (10).

22 Claims, 3 Drawing Sheets

U.S. PATENT DOCUMENTS

| | | | |
|---|---|---|---|
| 6,209,835 B1 * | 4/2001 | Walrath et al. | 248/276.1 |
| 6,361,570 B1 * | 3/2002 | Gow | 623/62 |
| 6,645,230 B1 * | 11/2003 | Whitehurst | 607/88 |
| 6,663,659 B1 * | 12/2003 | McDaniel | 607/88 |
| 6,854,862 B1 * | 2/2005 | Hopf | 362/220 |
| 2003/0088296 A1 * | 5/2003 | Waldmann | 607/88 |

FOREIGN PATENT DOCUMENTS

EP   1138349 A2   3/2001

* cited by examiner

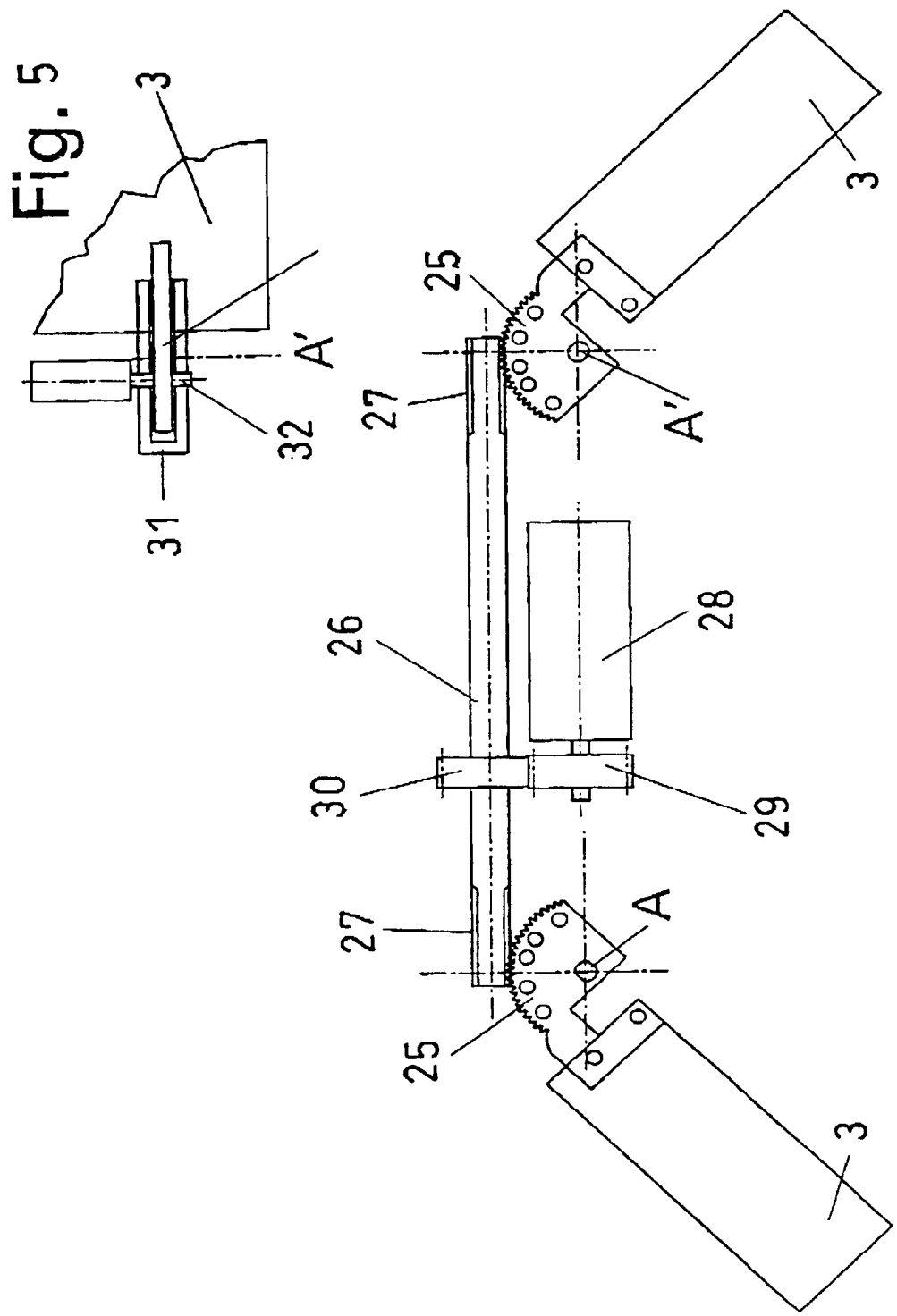

IRRADIATION APPARATUS AND SYSTEM, ESPECIALLY FOR PHOTODYNAMIC THERAPY

BACKGROUND OF THE INVENTION

Irradiation equipment, e.g., for photodynamic therapy, is known, which allows irradiation of the head and extremities of a patient from three sides. Irradiation equipment of a different type is provided for areal irradiation of the head, trunk or extremities of a patient.

However, no previous irradiation equipment is known that is suitable for both three-sided and areal irradiation.

SUMMARY OF THE INVENTION

Therefore, the goal of the invention is to design irradiation equipment, especially for photodynamic therapy, in such a way that it can be optimally used for three-sided irradiation and optimally used for areal irradiation.

The invention achieves this goal by designing the irradiation head with a middle section and two lateral leaves; mounted on opposite sides of the middle section in such a way that they can swivel to the side. The middle section is mounted by means of a first swivel joint in such a way that it can rotate on a swivel arm, such that the plane of rotation is parallel to the middle section. The swivel arm is mounted by means of a second swivel joint in such a way that it can rotate on a column, which is supported in a column support in such a way that it can be moved and locked. The axes of rotation of the middle section and the swivel arm are preferably perpendicular to each other; and the column support is preferably mounted on a control console or a wall.

The irradiation head of the irradiation equipment of the present invention consists of a middle section and two lateral leaves, which are mounted on opposite sides of the middle section in such a way that they can swivel to the side. The irradiation head can be formed into a plane surface that consists of the middle section and the two lateral leaves moved into a coplanar position with the middle section. By swiveling the lateral leaves, the flat surface can be continuously moved to form the shape of a rectangular U.

The middle section of the irradiation head is mounted in such a way that it can rotate, e.g., by means of a U-shaped stirrup on a first swivel joint placed at one end of a swivel arm. The plane of rotation is parallel to the surface of the middle section.

The other end of the swivel arm, which can be designed to telescope in and out, is mounted by means of a second swivel joint in such a way that it can rotate on a column, which can be moved in a column support and locked. The axis of rotation of the middle section of the irradiation head is perpendicular to the axis of rotation of the swivel arm.

The column support can be mounted, for example, on a control console or a wall.

In one embodiment of the invention, an operator control panel is installed on top of the control console.

In another embodiment of the invention, a projecting swivel support arm is provided on the control console to stabilize it against tipping. The control console can be equipped, e.g., with rollers or wheels, to make it possible to move the irradiation equipment of the invention quickly and easily to its place of use.

The column can be mounted, for example, so that it can rotate about its longitudinal axis in the column support.

The middle section and the lateral leaves of the irradiation head are preferably designed as rectangular plates, and radiation sources, e.g., light producers, are installed in or on the undersides of these plates. Examples of possible light producers are cylindrical fixtures or compact fixtures. The radiation sources are preferably interchangeable. The light producers have a spectrum from ultraviolet, through visible light, to infrared. A cooling device, e.g., a forced ventilator or vent, is preferably provided for cooling the radiation sources or light producers.

The mounting end of the lateral leaves is provided with, for example, toothed circular quadrants, which are arranged in such a way that they can rotate in a pivot located in the middle section. In addition, to adjust the lateral leaves, for example, each end of a shaft is provided with a worm. The worms move in opposite directions and engage the toothed quadrants of the lateral leaves. The shaft can be driven, for example, by an electric motor.

Alternatively, manual adjustment of the lateral leaves is possible. The lateral leaves are supported on a spindle of the middle section and can be locked in predeterminable positions by means of a pin.

The swivel joint, by which the middle section of the irradiation head is mounted on one end of the swivel arm, consists essentially of two mating joint parts. For centering purposes, one of the two parts of the joint has an extension that is pivoted in a corresponding recess of the other part of the joint. Details of this swivel joint are the object of Claims 9 to 12.

Electric lines for supplying power to the radiation sources or light producers run centrally through the first joint.

Since the irradiation head can be continuously or incrementally adjusted from a flat surface to a rectangular U shape, the irradiation equipment of the invention allows both areal irradiation and three-sided irradiation. In addition, since the irradiation head can be rotated about two perpendicular axes, and its height can be adjusted by moving the column, it can be optimally adapted to the individual anatomy of a patient. Areal irradiation of body regions, such as the head, the trunk, and the extremities, can be carried out with the irradiation equipment of the invention. Three-sided irradiation can also be carried out. As a result of the adjustment possibilities of the irradiation head, the patient can be placed in a standing, sitting, or lying position.

DESCRIPTION OF THE DRAWINGS

These and other objects of the present invention and the various features and details of the present invention are hereinafter more fully set forth with reference to the accompanying drawings, wherein:

FIG. 4 is a side view of an embodiment of an adjusting device for adjusting the lateral leaves of the irradiation head; and FIG. 5 is a section of an embodiment of a manually operated adjusting device for adjusting the lateral leaves of the irradiation head.

DESCRIPTION OF THE PREFERRED EMBODIMENTS

Figure 1:
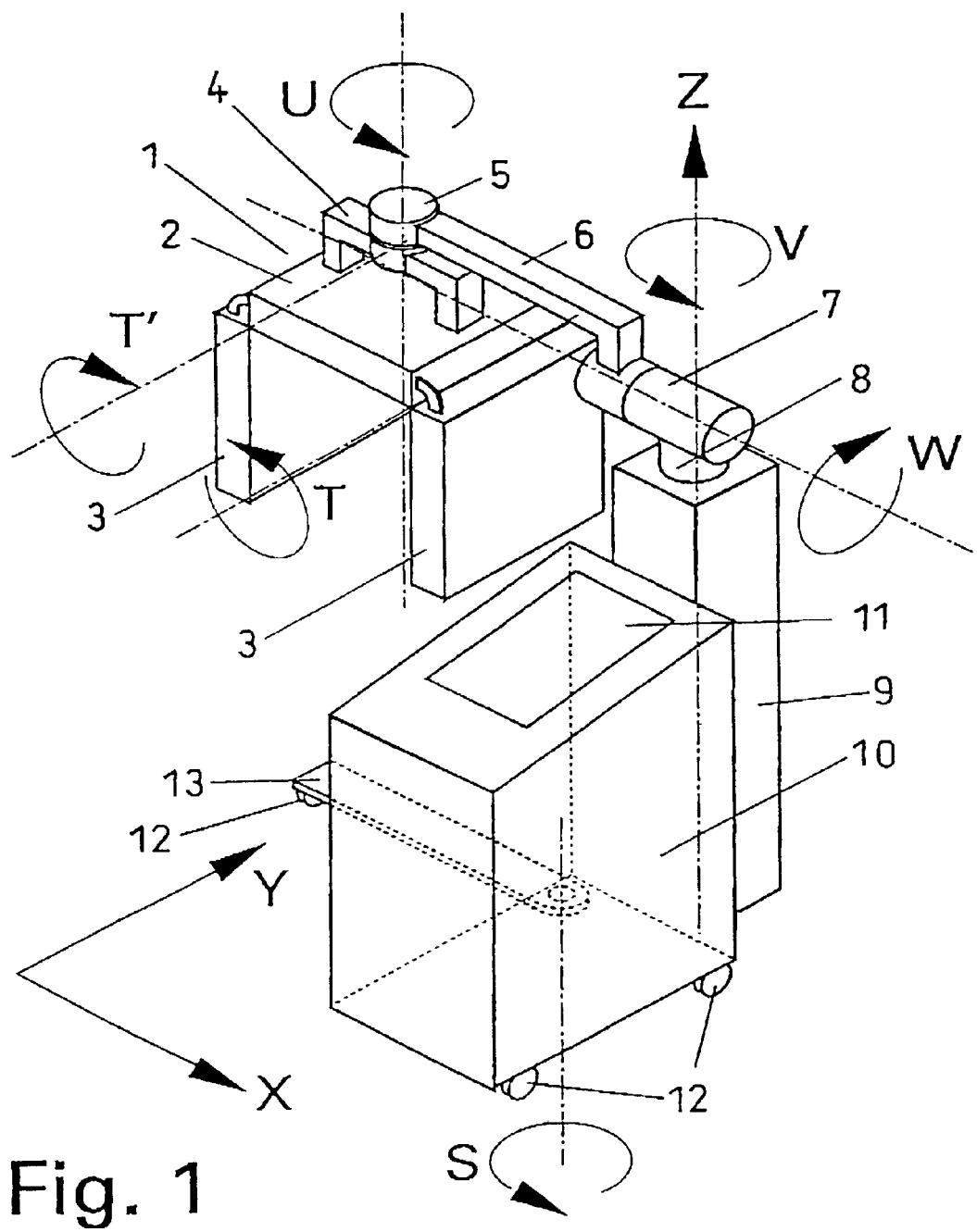
FIG. 1 is a perspective view of an embodiment of the irradiation apparatus & system of the present invention.

Referring now to the drawings and particularly to FIG. 1 thereof, there is shown an irradiation apparatus and system in accordance with the present invention comprising essentially of an irradiation head 1, a swivel arm 6, a column 8, a column support 9, and a control console 10.

The irradiation head 1 consists of a plate-shaped middle section 2 and two plate-shaped lateral leaves 3, which are mounted on opposite sides of the middle section 2 in such a way that they can be swiveled to the side. The lateral leaves 3 can be rotated about the axes T and T'. Together with the middle section 2, they can form a plane surface for areal irradiation. As has already been noted, the lateral leaves 3 can be rotated about the axes T and T', so that the irradiation head 1 can be changed from a plane surface to a rectangular U shape. This U shape of the irradiation head 1 is especially suitable for three-sided irradiation of the head and extremities of a patient, whereas the plane configuration is suitable for areal irradiation of the extremities or the trunk of a patient.

The radiation sources for irradiating a patient are installed in or on the undersides of the middle section 2 and the lateral leaves 3. For example, cylindrical fixtures or compact fixtures, which preferably are interchangeable, are used as radiation sources. These light producers have a spectrum from ultraviolet, through visible light, to infrared. For the sake of clarity, the light producers are not shown in FIG. 1.

The lateral leaves 3 can be rotated either manually or by an electric motor.

The upper side of the middle section 2 is mounted on the legs of a U-shaped stirrup 4, which in turn is mounted on a preferably telescoping swivel arm 6 by means of a swivel joint 5. The other end of the swivel arm 6, i.e., the opposite end from the swivel joint 5, is connected with the upper end of a column 8 by a swivel joint 7 in such a way that it can rotate 360°. The column 8 is supported in a column support 9 and can be moved along its center axis Z and rotated 360° about its center axis Z in direction of rotation V. The column 8 can be locked in any desired position in the column support 9, which is mounted on the rear wall of a control console 10. Alternatively, the column support 9 can be mounted on a wall of a treatment room. The control console 10, which has an operator control panel 11 installed in its upper surface, is equipped with rollers or wheels 12 on its base to make it easier to move. To increase the stability of the control console 10, a support arm 13 is provided on the underside of the control console. The support arm 13 can, for example, be pulled out or rotated in direction S. The irradiation head 1 can be rotated, on the one hand, about axis U and axis Z, which is parallel to axis U, and, on the other hand, about axis W, which is perpendicular to axes U and Z. Furthermore, the irradiation head 1 can be adjusted to any height. The range of rotation about axes U, Z, and W can be 360° or can be limited to a predetermined value by stop devices.

Since the irradiation head 1 can be adjusted in height along axis Z and rotated about axes of rotation U, W, and Z, and its lateral leaves can be rotated about axes T and T', it can be optimally adapted to the individual anatomy of a patient.

The power supply lines for the light producers in the middle section 2 and the lateral leaves 3 run from the control console 10 through the centers of the swivel joint 7, the swivel arm 6, the swivel joint 5 and the U-shaped stirrup 4 to the light producers.

Figure 3:
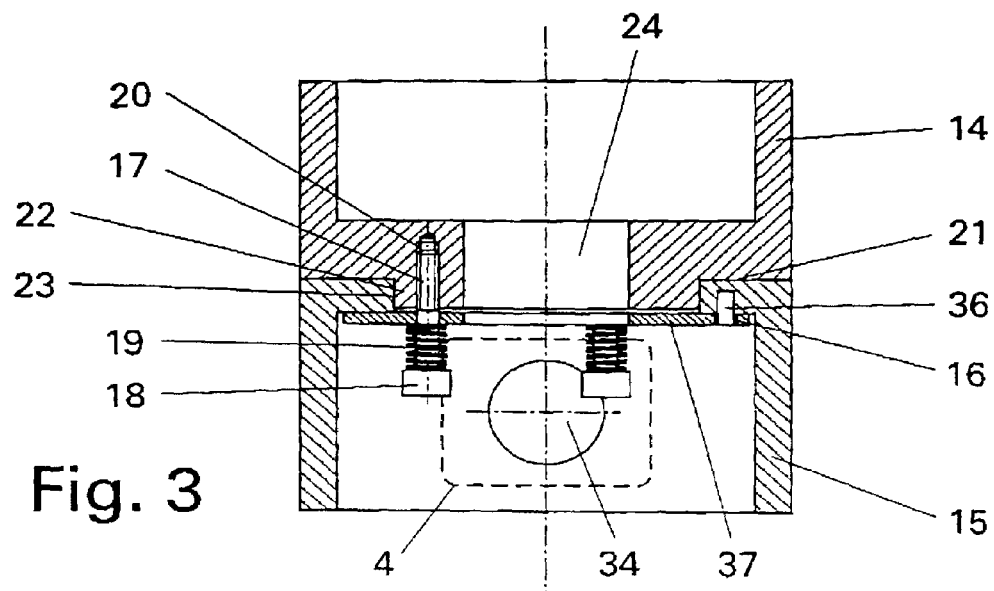
FIG. 3 is a longitudinal section through the joint in FIG. 2.
Figure 2:
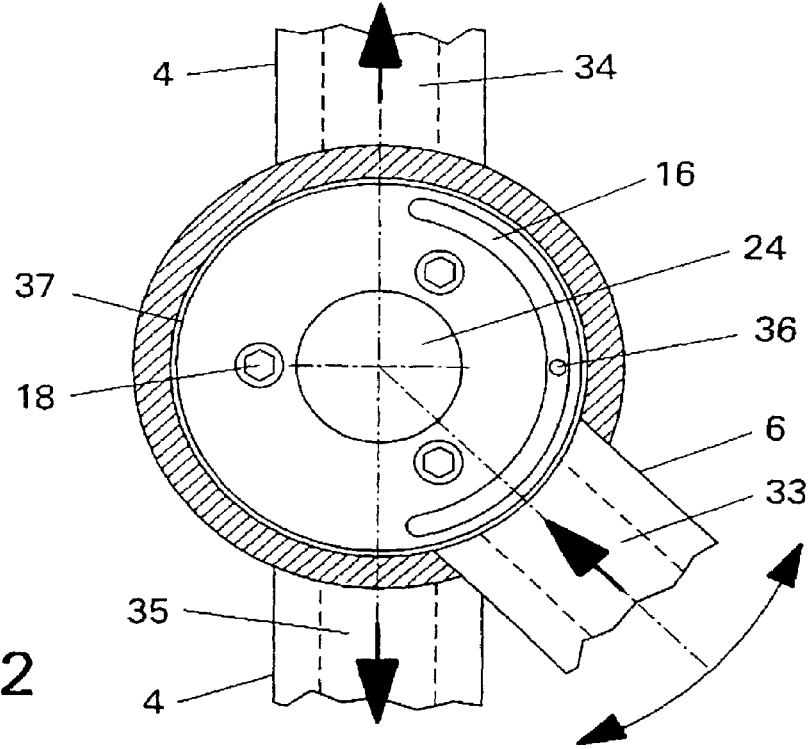
FIG. 2 is a top view of an embodiment of a joint for mounting the irradiation head on the swivel arm.

FIG. 2 shows a top view of the swivel joint 5, and FIG. 3 shows a longitudinal section through swivel joint 5.

The swivel joint 5 consists of an upper joint part 14 with an extension 22 and a lower joint part 15 with a recess 23, into which the extension 22 fits. A disk 37 is attached to the extension 22 by screws 17. The disk 37 is dimensioned in such a way that its radially outer ring surface, which extends beyond the extension 22, is frictionally engaged with the collar part that bounds the recess 23 of the lower part 15 of the joint. In this way, the joint parts 14 and 15 are joined in such a way that they are axially fixed but can be rotated in the peripheral direction. Rotatability is limited by a stop pin 36, which is fastened to the lower part 15 of the joint and engages an opening 16, which has the shape of a circular segment, in the disk 37.

As is shown especially in FIG. 3, spring elements in the form of compression springs 19 are placed between the heads 18 of the screws 17 and the disk 37. This design allows variation of the contact pressure acting on the disk 37, by which the friction torque can be set or adjusted as desired. Instead of the helical spring 19 shown here, a disk spring may be used as the spring element.

The power supply lines for the light producers, which, for the sake of clarity, are not shown in FIGS. 2 and 3, pass through the central opening 24 of the two parts 14 and 15 of the joint.

The power supply lines for the light producers pass through a central cable duct 33 of the swivel arm 6, through the central openings 24 of the upper part 14 and the lower part 15 of the swivel joint, and through the central cable ducts 34 and 35 of the U-shaped stirrup 4. The arrows indicate the course followed by the power lines.

FIG. 4 shows a side view of the adjusting device for adjusting the lateral leaves of the irradiation head.

The upper end of each lateral leaf 3 is provided with a toothed quadrant 25, which is mounted on the middle section 2 in such a way that it can rotate about a pivot A or A'. The pivots A and A' correspond to the axes of rotation T and T'. Each end of a shaft 26 has a worm 27. One of the worms 25 engages one of the toothed quadrants 25, and the other worm 27 engages the other toothed quadrant 25. The two worms 27 move in opposite directions. The gear 29 of an electric motor 28 drives a gear 30 seated on the shaft 26. The lateral leaves 3 can thus be adjusted by the electric motor 28.

FIG. 5 shows a section of a manual adjusting device for adjusting the lateral leaves of the irradiation head.

On each side, a lateral leaf 3 is supported in a bearing 31 in the middle section 2. The lateral leaves can be locked by means of a pin 32 that can be inserted through a bore in the bearing 31 and through bores in the toothed segment 25.

As has already been mentioned, the irradiation equipment can be optimally adapted to the varied anatomies of patients, because the irradiation head and its lateral leaves can be rotated about five axes, and its height can also be adjusted. Interchange of the radiation sources makes it possible to use the radiation source that is therapeutically optimal for each patient.

The embodiment of the irradiation equipment of the invention shown here is designed in such a way that it can be changed from its operating position, which allows a large number of adjustments, to a space-saving park position. For this purpose, the swivel arm that supports the irradiation head and the support arm that stabilizes the equipment can each be swivelled in by 90° about a vertical axis.

LIST OF REFERENCE SYMBOLS 1 irradiation head
2 middle section of the irradiation head
3 lateral leaf
4 U-shaped stirrup
5 swivel joint 6 swivel arm
7 swivel joint
8 column
9 column support
10 control console
11 operator control panel
12 wheel
13 support arm
14 upper part of the swivel joint
15 lower part of the swivel joint
16 opening
17 screw
18 screw head
19 spring element
20 taphole
21 friction surface
22 extension
23 recess
24 central opening
25 toothed quadrant
26 shaft
27 worm
28 electric motor
29 gear
30 gear
31 bearing
32 pin
33 central cable duct of the swivel arm
34 central cable duct of the U-shaped stirrup
35 central cable duct of the U-shaped stirrup
36 stop pin
37 disk
A pivot
A' pivot
S axis of rotation
T axis of rotation
T' axis of rotation
U axis of rotation
V axis of rotation
W axis of rotation
Z axis of rotation

The invention claimed is:

1. Irradiation apparatus particularly adapted for photodynamic therapy, comprising an irradiation head (1) equipped with radiation sources including a middle section (2) and two lateral leaves (3) mounted on apposite sides of the middle section (2) in such a way that they can swivel to the side; said middle section (2) being mounted on a swivel arm (6) by means of a first swivel joint (5) in such a way that it can rotate, so that the axis of rotation (U) 16 perpendicular to the middle section (2); said swivel arm (6) being mounted on a column (8) by means of a second swivel joint (7) in a predetermined orientation to rotate about an axis (W); the axis of rotation (U) of the middle section (2) and the axis of rotation (w) of the swivel arm (6) being perpendicular to each other column, (8) being supported in a column support (9) in such a way that it can be moved along its central axis (Z) and locked, a toothed segment (25) supported in a pivot (A, A') mounted on the middle section (2) on each side of the middle section (2); and a shaft (26) driven by an electric motor (28) provided with a worm (27) at each end of the shaft (26) to adjust the lateral leaves (3); wherein the worms (27) move in opposite directions; and each worm (27) engages one of the toothed segments (25).

2. Irradiation apparatus in accordance with claim 1 wherein the swivel arm (6) can be pulled out and adjusted to predeterminable length.

3. Irradiation apparatus in accordance with claim 1, wherein the middle section (2) and the lateral leaves (3) of the irradiation head (1) are designed as rectangular plates, and wherein the radiation sources are installed in or on the undersides of these plates.

4. Irradiation apparatus in accordance with claim 1 wherein the two lateral leaves (3) can be swivelled at least 90° from the plane of the middle section (2), so that the irradiation head (1) can be adjusted from a plane surface, formed by the middle section (2) and the extended lateral leaves (3), to a rectangular U shape, formed by the middle section (2) and the lateral leaves (3) swivelled 90° from their extended position.

5. Irradiation apparatus in accordance with claim 1 wherein the lateral leaves (3) are supported at the upper end in a bearing (31) of the middle section (2) in such a way that they can be manually adjusted, and that they can be locked in a predetermined portion by a pin (32) in the bearing (31).

6. Irradiation apparatus in accordance with claim 1 wherein the middle section (2) of the irradiation head (1) is mounted on the first swivel joint (5) by a U-shaped stirrup (4).

7. Irradiation apparatus in accordance with claim 1 wherein the first swivel joint (5) consists of a lower joint part (15) and an upper joint part (14) supported on it in such a way that it can rotate; said two parts (14, 15) of the joint being joined by a disk (37) that is screwed onto the upper part (14) of the joint and is supported on the lower part (15) of the joint in such a way that the two parts (14, 15) of the joint are axially fixed but are able to rotate to a limited extent; and an opening in the form of a circular segment, into which a stop pin (36) provided on the lower part (15) of the joint in the disk fits.

8. Irradiation apparatus particularly adapted for photodynamic therapy, comprising an irradiation head (1) equipped with radiation sources including a middle section (2) and two lateral leaves (3) mounted on opposite sides of the middle section (2) in such a way that they can swivel to the side; said middle section (2) being mounted on a swivel arm (6) by means of a first swivel joint (5) in such a way that it can rotate, so that the axis of rotation (U) is perpendicular to the middle section (2); said swivel arm (6) being mounted on a column (8) by means of a second swivel joint (7) in a predetermined orientation to rotate about an axis (W); the axis of rotation (U) of the middle section (2) and the axis of rotation (w) of the swivel arm (6) being perpendicular to each other column (8) is supported in a column support (9) in such a way that it can be moved along its central axis (Z) and locked, the first swivel joint (5) consists of a lower joint part (15) and an upper joint part (14) supported on it in such a way that it can rotate; said two parts (14, 15) of the joint being joined by a disk (37) that is screwed onto the upper part (14) of the joint and is supported on the lower part (15) of the joint in such a way that the two parts (14, 15) of the joint are axially fixed but are able to rotate to a limited extent; and an opening in the form of a circular segment, into which a stop pin (36) provided on the lower part (15) of the joint in the disk fits.

9. Irradiation apparatus in accordance with claim 8, wherein one part (14) of the joint has an extension (22), and the other part (15) of the joint has a corresponding recess (23) for receiving the extension (22) for centering purposes and to lock the joint in the axial direction, at the mating ends of the two parts (14, 15) of the joint.

10. Irradiation apparatus in accordance with claim 8 wherein the disk (37) is fastened to the upper part (14) of the joint by screws (17); and wherein the outer edge of the disk

(37) is frictionally engaged with a collar part that bounds the recess (23) of the lower part (15) of the joint; and including a spring element (19) on at least one of the screws (17) between the head (18) of the screw and the disk (37) to permit adjusting the friction torque.

11. Irradiation apparatus in accordance with claim 10, wherein the spring element is a helical spring (19).

12. Irradiation apparatus in accordance with claim 10, wherein the spring element is a disk spring (19).

13. Irradiation apparatus in accordance with claim 8 wherein the electric lines for supplying power to the radiation sources pass through a central opening of the second swivel joint (7), a central cable duct (33) of the swivel arm (6), a central opening (24) of the first swivel joint (5), and two central cable ducts (34, 35) of the U-shaped stirrup (4).

14. Irradiation apparatus in accordance with claim 8 wherein the radiation sources are interchangeable.

15. Irradiation apparatus in accordance with claim 8 wherein light producers are used as the radiation sources.

16. Irradiation apparatus in accordance with claim 15 wherein cylindrical or compact fixtures are used as the light producers.

17. Irradiation apparatus in accordance with claim 15 wherein light producers with a spectrum from ultraviolet, through visible light, to infrared are provided.

18. Irradiation apparatus in accordance with claim 8 wherein the control console (10) can be moved by wheels (12) or rollers mounted on its base.

19. Irradiation apparatus in accordance with claim 8 including a control console (10) equipped with a support arm (13) that can be swivelled out or pulled out to stabilize the control console (10).

20. Irradiation apparatus in accordance with claim 8 including an operator control panel (11) installed on the top of the control console (10).

21. Irradiation apparatus in accordance with claim 8 including a cooling device for cooling the radiation sources.

22. Irradiation apparatus in accordance with claim 8 including a control console (10) having a support arm (13 and wherein the swivel arm (6) which supports the irradiation head (1) can be swivelled 90° about the vertical axis (Z), and the support arm (13) can be swivelled 90° about the vertical axis (S) to place the equipment in a space-saving park position.

* * * * *